United States Patent [19]

Boshoff

[11] 3,981,398
[45] Sept. 21, 1976

[54] AID IN THE MANAGEMENT OF CLINICAL EMERGENCIES IN MEDICAL AND DENTAL PRACTICES AND OTHER CIRCUMSTANCES

[75] Inventor: Pieter Nico Sinclair Boshoff, Pretoria, South Africa

[73] Assignee: Hendrik Lukas Pienaar, Verwoerdburg, South Africa

[22] Filed: Jan. 29, 1975

[21] Appl. No.: 545,190

[30] Foreign Application Priority Data
Sept. 13, 1974 South Africa.................... 74/5849

[52] U.S. Cl................................ 206/223; 206/232; 206/803; 35/17
[51] Int. Cl.²................... B65D 69/60; G09B 23/28
[58] Field of Search................ 206/803, 232, 223; 35/7 R, 7 A, 28.3, 17, 50, 53; 281/38

[56] References Cited
UNITED STATES PATENTS

| | | | |
|---|---|---|---|
| 1,644,830 | 10/1927 | Henderson | 206/223 |
| 2,201,888 | 5/1940 | Deutsch | 35/28.3 |
| 2,874,707 | 2/1959 | Koppel | 206/223 |
| 3,191,319 | 6/1965 | Waisgerber | 35/53 R |
| 3,704,529 | 12/1972 | Cioppa | 35/17 |
| 3,719,801 | 3/1973 | Drexler | 35/17 |

*Primary Examiner*—George E. Lowrance
*Assistant Examiner*—Douglas B. Farrow
*Attorney, Agent, or Firm*—Millen, Raptes & White

[57] ABSTRACT

The apparatus for use especially in treatment of emergency medical conditions. The apparatus comprises a briefcase or the like containing a holder, preferably a tray-like receptacle with recesses containing a drug or instrument or other article in each recess, in combination with preferably a plurality of masks. Each mask is adapted to mask the holder and its contents except for openings in the mask which expose same, but not all of the articles in the holder, the exposed articles being appropriate to a particular mode of treatment of the person, the mask being marked to indicate that particular treatment at least. Preferably, the mask also carried step-by-step instructions to confirm diagnosis and carry out appropriate treatment, with the articles located in sequential order related to the next.

9 Claims, 5 Drawing Figures

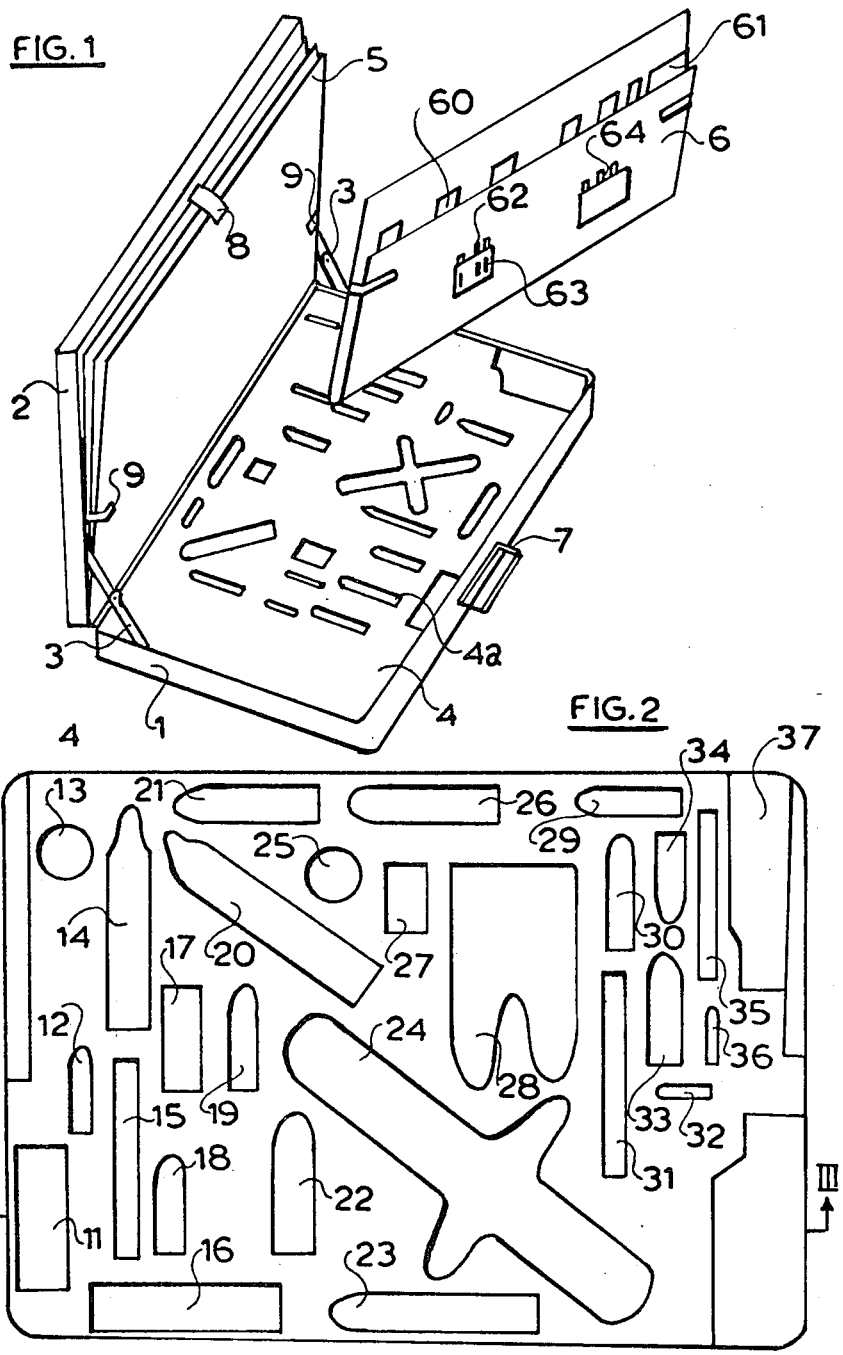

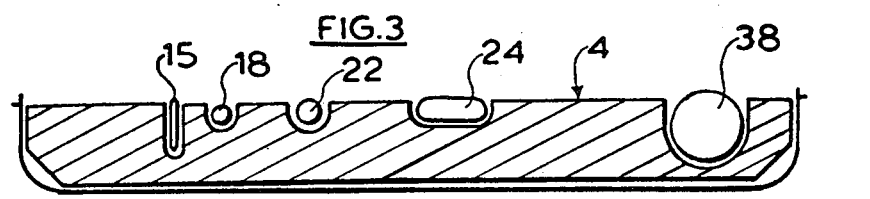
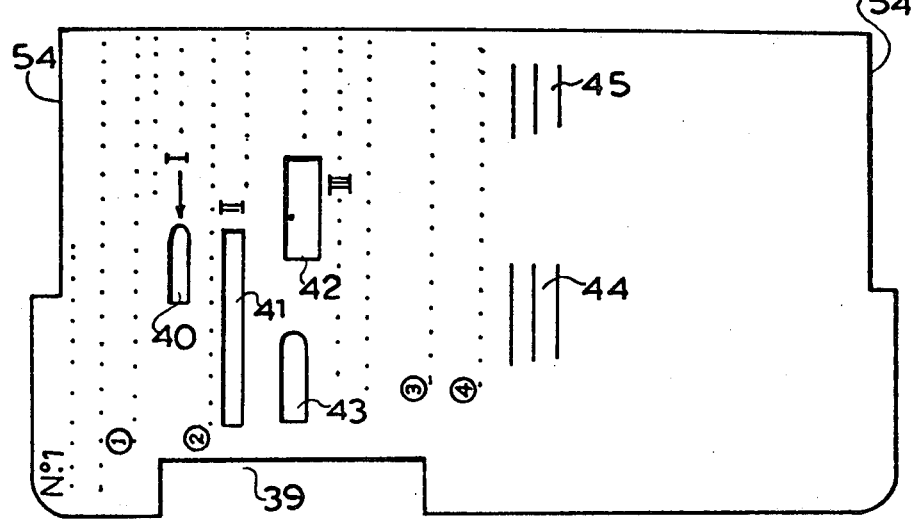
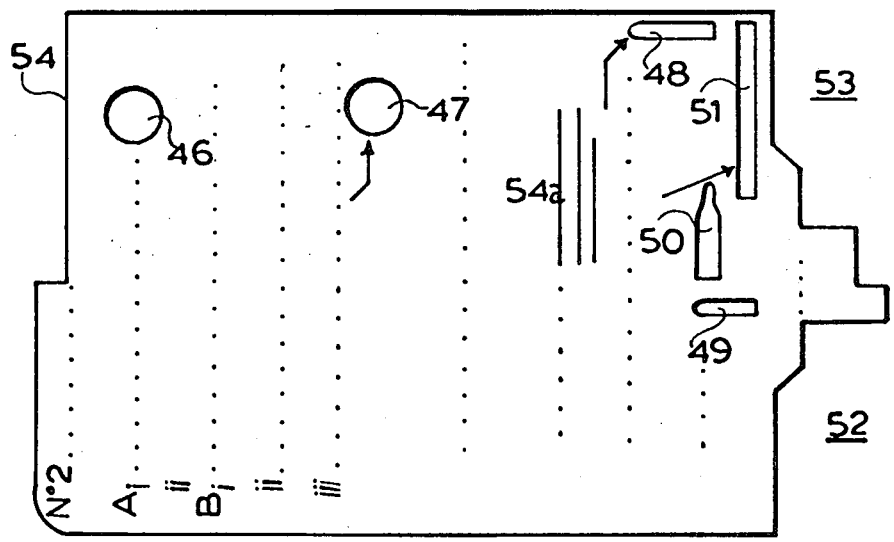

AID IN THE MANAGEMENT OF CLINICAL EMERGENCIES IN MEDICAL AND DENTAL PRACTICES AND OTHER CIRCUMSTANCES

BACKGROUND OF THE INVENTION

This invention concerns an aid for use in the management of clinical and other emergencies in which the life of a person is endangered, for example, in medical and dental practices. The invention provides a means for use as an aid to memory and as a convenient supply of essential medical instruments and drugs for use in the management of clinical and other emergencies in which a person's life is placed in danger. The invention furthermore provides a method of furnishing an aid to memory and a supply of medical instruments and drugs for use in such circumstances.

As is well-known, there are a number of medical conditions which can arise in a person, which can be classified as emergencies in the sense that they involve an immediate or sometimes delayed, danger to the life of that person. Merely as examples, can be cited such conditions as heart attacks of a severe degree, cardiac arrest or drug-induced asthma or angioneurotic oedema. A common factor in many such emergencies is that the supply of oxygenated blood to the brain is critically diminished or interrupted, and, in these circumstances and other emergencies, death of the person is imminent, and immediate treatment of the appropriate kind must be administered. This type of situation frequently demands the utmost calmness and efficacy in the person administering the treatment and a ready supply of the medical instruments and drugs necessary. Now it is well known that such emergencies can occur in medical and dental circumstances, for example, a person undergoing routine treatment in a dental surgery may suffer a severe medicinally induced asthmatic attack, or a similarly induced angioneurotic oedema. Cardiac arrest in the dental chair has been frequently reported in the literature. It is an unfortunate but almost universal fact that such situations have a powerful capacity to induce extreme nervousness in a person who has to deal with such an emergency, and of course such nervousness severely militates against those very qualities which are necessary for the most effective treatment of the emergency. Not only this factor, but the necessary medical instruments and drugs must be immediately to hand. Doctors, dentists, nursing sisters and other para-medical persons are not immune to these difficulties when confronted with the management of such emergencies, and even the most competent practitioner will frequently have to resist a tendency to become very nervous, or even panic-stricken, or they may not have emergency drugs and equipment immediately to hand.

Objects of providing the means in accordance with this invention thus include the following:
a. to save the patient's life,
b. to keep the practitioner calm enough to be capable enough to do so,
c. to train medical or dental personnel in emergency procedures, and
d. where necessary, to enable a layman to assist the practitioner after a brief scanning of the instructions, (or even to perform at least some procedures himself).

SUMMARY OF THE INVENTION

Means in accordance with this invention, comprises any holder for a variety of articles, which are useful in the treatment of persons, the holder being adapted to hold each particular article in a particular position; in combination with at least one mask, which is adapted to be placed in a particular position to mask the holder, the mask having openings in its surface which are adapted to expose some, but not all of the articles when they are in the holder, which articles are appropriate to a particular mode of treatment of the person, the mask being marked to indicate that particular treatment.

Thus, a plurality of different masks may be provided, each mask being appropriate to a different treatment for a different emergency condition. Each mask will expose only those articles such as instruments and drugs which are appropriate to the treatment of the condition concerned.

Preferably, the openings in each mask are arranged in a manner adapted to expose the articles in a sequence from top to bottom of the mask, which corresponds substantially with the order in which the articles which are exposed by the openings, will be used.

Preferably, these openings in the mask are combined with a text relating to the particular treatment. For example, the text may comprise a description of the condition for which the mask is appropriate, a note of causes, an aid to diagnosis and directions for carrying out the appropriate treatment.

It is convenient if a means in accordance with this invention is built into a briefcase or the like, so that it is adapted to be conveniently portable. The means may then comprise a tray-like receptacle with recesses for the articles, including instruments and drugs, a container for needles, syringes and further ancillary articles, masks in the form of flat cards which can cover the receptacle, adapted to be useful as guides for the various types of treatment, and to expose appropriate drugs and instruments and if desired, a further chart illustrating and describing physical methods of treatment.

The portable means particularly may comprise devices adapted to ensure that articles do not become displaced, e.g. by coming out of the recesses. Such device can be a cover, either in the form of a breakable seal, e.g. clear plastic film, or a replaceable lid, again preferably transparent. Alternatively, the articles can be pressed tightly into holding recesses made of a resilient material; hooks, clips and bands are another general kind of device which may serve the same retentive purpose.

Preferably, the masks are adapted so that they can only be placed in the correct orientation to mask the receptacle, and cannot easily be inadvertently placed the wrong way around. Thus, the mask periphery can be asymmetrically shaped so that it only fits one way (with text uppermost). Or, there can be locating holes and pins, a prominent colour code on the edges of the mask, to be matched with a corresponding colour code on the receptacle. A more elaborate arrangement would be to mechanically link the masks to the receptacle, the linkage being adapted to permit any one mask to be selected and moved into a "masking" position but to ensure that the mask is then correctly orientated.

A method of furnishing an aid to memory in the context of treatment of persons suffering from emergency medical conditions, in accordance with this invention, comprises providing a receptacle having a plurality of recesses in specified positions for medical instruments and drugs, packing the appropriate medical instruments and drugs into the appropriate recesses into the receptacle and providing at least one mask for a particular treatment which has openings in the mask in appropriate positions to indicate those medical instruments and drugs which are appropriate to the particular treatment.

BRIEF DESCRIPTION OF THE DRAWINGS

This invention will be more fully described by way of example, the example being a preferred embodiment of the invention, which is illustrated in the accompanying drawings, in which:

FIG. 1 is a perspective view of the means,

FIG. 2 is a plan view of the receptacle forming part of the means,

FIG. 3 is a section of sec. III—III of FIG. 2,

FIG. 4 is a plan view of the mask, forming part of the means and

FIG. 5 is a plan view of a further mask, forming a part of the means.

DESCRIPTION OF THE PREFERRED EMBODIMENT

The means in accordance with the preferred embodiment of this invention is in the form of a briefcase or similar container which contains all of the components.

As shown in FIG. 1 the briefcase 1 can be conveniently opened by lifting the lid 2, and hinges 3 hold the lid conveniently upright. The briefcase comprises, in the first place, a receptacle 4 which has recesses 4a for various instruments and drugs. In the receptacle in use are packed the instruments and drugs, each instrument and each drug being placed in its own particular recess. In the lid 2 of the briefcase is provided a set of masks 5 (in this example eight in number), a descriptive or explanatory chart for the means as a whole and a chart which is fixed or attached to the inside of the lid, and which describes various physical methods of treatment in various emergency situations. Also retained in the lid, when the briefcase is closed is a wallet 6, which carries supplies of various medical instruments. The handle 7 of the briefcase of course facilitates transporting the means as a whole. Tag 8 is provided to facilitate removal of the masks and brackets 9 are hingedly connected to lid 2 of the briefcase, so that in one position they may retain the masks 5 and the wallet 6 in the lid 2, while when hinged away to another position, they permit removal of these things.

Referring to the receptacle 4 in more detail, with reference to FIG. 2 and FIG. 3, this as shown comprises a plurality of recesses, which are each adapted to contain a particular medical instrument or drug. The various medical instruments and drugs which are to be retained in the recesses are indicated overleaf.

| NO. | PHARMACOLOGICAL/ THERAPEUTIC CLASSIFICATION: | GENERIC NAME: | EG. OF TRADE NAME: |
| --- | --- | --- | --- |
| 11 | ANTI-SNAKEBITE SERUM AND SCORPION ANTI-VENOM | — | EX SOUTH AFRICAN INSTITUTE OF MEDICAL RESEARCH (S.A.I.M.R.) |
| 12 | SYMPATHOMIMETICS | ADRENALIN INJECTION Bp | ADRENALIN |
| 13 | VASODILATORS | GLYCERAL-TRINITRATE TABLETS | ANGISED |
| 14 | — | DEXTROSE INJECTION Bp | — |
| 15 | — | — | BUTTERFLY NEEDLES |
| 16 | BRONCHODILATOR | SALBUTAMOL | VENTOLIN INHALER |
| 17 | CORTICO STEROID | HYDROCORTISONE SODIUM SUCCINATE | SOLUCORTEF |
| 18 | ANTIHISTAMINIC | PROMETHAZINE HYDROCHLORIDE INJECTION | PHENERGAN |
| 19 | ANTIHISTAMINIC | MEPYRAMINE | ANTHISAN |
| 20 | — | DEXTROSE INJECTION Bp | — |
| 21 | SYMPATHOMIMETIC | METHOXAMINE-HYDROCHLORIDE | VASOXINE |
| 22 | BRONCHODILATORS | THEOPHYLLINE ETHYLENE DIAMINE | AMINOPHYLLIN |
| 23 | TRANQUILIZERS | DIAZEPAM | VALIUM |
| 24 | — | ORAL TUBE FOR MOUTH TO MOUTH RESUSCITATION | — |
| 25 | VASODILATOR | GLYCERAL-TRINITRATE TABLETS | ANGISED |
| 26 | — | — | PHIAL WATER FOR INJECTIONS |
| 27 | CORTICOIDS | 2ml HYDROCORTISONE SODIUM SUCCINATE | SOLUCORTEF |
| 28 | — | 4 × 50ml PHIALS OF SODIUM BICARBONATE | — |
| 29 | — | 2 × 1ml PHIALS PENTAZOCINE | SOSEGEN |
| 30 | — | 1 × 10ml PHIAL CALCIUM-CHLORIDE | — |
| 31 | — | EMERGENCY TRACHEAL CATHETER | — |
| 32 | — | 1 × 1ml PHIAL OF ATROPHINE SULPHATE | — |
| 33 | — | 1 × 10ml PHIAL OF WATER FOR INJECTIONS | — |
| 34 | — | 1 × 1ml PHIAL OF ADRENALIN | — |
| 35 | — | 1 × STERILE INJECTION NEEDLE | BUTTERFLY |
| 36 | — | 1 × 1ml PHIAL ATROPHINE | — |
| 37 | — | 1 × 150ml BOTTLE NORMAL SALINE FOR ADMINISTRATION BY VENOCLYSIS | — |
| 38 | — | 1 × 150ml BOTTLE SODIUM CHLORIDE AND DEXTROSE INJECTION FOR ADMINI- | — |

| NO. | PHARMACOLOGICAL/ THERAPEUTIC CLASSIFICATION: | GENERIC NAME: | EG. OF TRADE NAME: |
|---|---|---|---|
| | STRATION BY VENOCLYSIS | | |

Each recess in the receptacle is sized and shaped to snugly accommodate each article or articles intended for it. The recesses are furthermore adapted so that the articles contained in them cannot fall out and become confused when the briefcase is carried or otherwise handled.

The wallet 6 contains a selection of syringes for injections, for example, several 2ml, 5ml, 10ml and 20ml syringes, 60.

There is furthermore a venoclysis set 61, a number of files 63 to assist in severing the necks of phials, adhesive strips 62 and a selection of injection needles 64.

FIG. 4 illustrates the first of the masks, which is applicable in a case of medicinally induced asthma. This mask has aperture 39 to expose the Ventilon inhaler 16, aperture 40 to expose the adrenalin 12, aperture 41 to expose the intravenous butterfly needle 15, aperture 42 to expose the Solucortef 17 and aperture 43 to expose the Aminophyllin 18. The text of Chart No. 1 reads as follows:

No. 1 MEDICINALLY INDUCED ASTHMA

Causes

This is an allergic manifestation, e.g. a reaction to salycilates or local anaesthetic solution, etc.

Diagnosis

Dyspnoea; easier inhalation than expiration; wheezing or stridor.

Treatment i. If the asthmatic attack is light, try to break it with the Ventolin inhaler (an arrow points out the Ventolin aperture 39). Follow step 2 if relief is not almost immediate.
ii. If attack is severe
  a. inject subcutaneously Adrenalin 1:1000 at rate of 1/10th ml per minute until attack is eased or 1 ml is given (0.5ml for children). (Here an arrow points out the aperture 40 for Adrenalin);
  b. place an intravenous butterfly needle and secure with adhesive strip. Through this, inject 100mg Solucortef. (Here an arrow points to the aperture 42 for Solucortef);
  c. inject 250mg Aminophyllin slowly by intravenous route. (Here an arrow points out the aperture for 43 Aminophyllin).
iii. Monitor pulse
  If it disappears, follow procedures set out under mask No. 5 — cardiac arrest.
iv. If these drugs do not relieve the patient, contact a medical practitioner urgently, or arrange for transfer to a hospital. (Here the names and addresses of medical practitioners are indicated at 44 and the telephone numbers for ambulances at 45).

Thus, the masks and the receptacle combine to facilitate the execution of treatment in a calm and methodical way. The text and the drugs exposed by the apertures provide an aid to memory, or in the case of paramedical personnel or even completely untrained people, instructions for performing at least the simpler technical procedures, thus being of positive assistance to the practitioner (and the patient) involved. Techniques such as intravenous injections can naturally usually only be carried out by trained personnel, and the preferred embodiment of the invention here described, is intended for dentists, doctors, nursing sisters and people of similar medical training. Nevertheless, the means could be used by others in the capacity of assistants or even alone as the occasion demands, at least insofar as the less skilled techniques are concerned, e.g. mouth to mouth resuscitation.

FIG. 5 illustrates the mask No. 2, which is selected when Angina Pectoris and/or Myocardial infarction are diagnosed. This chart has an aperture 46 to expose the glyceryl-trinitrate tablets 13, and an aperture 47 to expose the second container of glyceryl-trinitrate tablets 25, an aperture 48 to expose the Sosegen 29, apertures 49 and 50 to expose the Athropin and water 32 and 33, respectively, and an aperture 51 to expose the butterfly needle 35. Apertures 52 and 53 further expose the bottles 38 and 37, respectively, for intravenous drip.

The text (chart No. 2) reads as follows:

No. 2 ANGINA PECTORIS AND/OR MYOCARDIAL INFARCTION a. An Angina Pectoris attack i. Stop all dental treatment;
ii. Place an 0.6mg tablet of glycerol-trinitrate under the patient's tongue.

b. Myocardial infarction i. Stop all dental treatment and differentiate between an Angina attack and Myocardial infarction:
  1. Angina rarely lasts longer than 10 minutes after effort is ceased, or recommended drug is used;
  2. Myocardial infarction produces a grey pallor, nausea, dyspnoea, sweating and even cardiac arrest.
ii. Place an 0.6mg tablet of glycerol-trinitrate under patient's tongue. If pain is not relieved, place a second tablet under the tongue. Do not exceed two tablets. (Here an arrow points out the aperture 47).
iii. If after 15 minutes, the pain is not relieved, assume that infarction has occurred and do the following:
  1. Put the stool in a 45° position. If the patient is badly shocked, place him in shock position. This will accommodate cerebral blood supply;
  2. Administer oxygen at 4 to 5 l per minute. Phone the patient's medical doctor for instructions. If unknown, contact either of the following:
  (Here the names and telephone numbers of two doctors who have previously been entered, are indicated at 54a);
  3. If help is not immediately available, inject 1 to 1½ ampoules of Sosegen intramuscularly. (Here an arrow points out the aperture 48).

This will serve as an analgesic until the patient is transferred to hospital, or until a medical practitioner can take over. In both instances, inform that this drug was administered.

4. Monitor the patient's pulse. If it disappears follow procedure set out in No. 5 (cardiac arrest). If the pulse rate goes below 50 per minute —

Mix 0.6mg Athropin and 3ml water. Place an intravenous butterfly needle. Inject through this, 1ml mixture. If pulse does not improve, inject a further 1ml. (Here an arrow points out the apertures 49, 50 and 51 for the Athropin, water and intravenous butterfly needle, (respectively). The apertures 52 and 53 expose the bottles for setting up the intravenous drip.

In the embodiment, the masks shown in FIGs. 4 and 5 are illustrated with inset edges 54. These serve the important function of ensuring the correct orientation of the mask when the user places the mask face-up over the receptacle for the instruments and drugs. The inset 54 accommodates the hinges 3, and if an attempt is made to place the mask the wrong way around, the hinges will interfere and prevent this.

Naturally, many other adaptations of the masks can be resorted to to ensure the correct orientation of the mask when it is used.

In a similar manner, further masks are provided for further conditions. These are summarized in the following:

MASK No. 3 — ANGIO-NEUROTIC OEDEMA

Causes

Mostly due to a penicillin sensitivity reaction. Any drug can trigger off such a reaction.

Diagnosis

Hoarseness. Usually takes the form of acute swelling of the face, eyelids and lips. Any part of the body, e.g. testes may be involved. Glottis-oedema may complicate matters.

Treatment i. Inject subcutaneously 0.5ml Adrenalin 1:1000 solution (0.25ml for children). (Aperture for Adrenalin 12).
ii. Place an intravenous butterfly needle and secure it with an adhesive strip. (Aperture for needle 15).
iii. By this intravenous route, inject the following: 1 and 2.
   1 — (Aperture for Phenergan 18)
   2 — (Aperture for Solucortef 17);
iv. Give a prescription for Phenergan tablets, namely, 10–25mg BID for 2 days;
v. Warn patient of the drowsiness produced by these anti-histaminic drugs;
vi. If suffocation (Glottis-oedema) is present:
   a. Summon medical assistance. (Here the names and telephone numbers of two doctors who have previously been entered, are indicated);
   b. If not immediately available — Perform an emergency Laryngostomy: Feel with a fingertip for the notch between the thyroid and crycoid cartilages. Push the catheter through this thin membrane at an angle of 45°, so as to avoid the vocal cords. If unsure of your landmarks, perform an emergency tracheostomy. (See lid of the briefcase for instructions for this method). (Here an aperture is provided for the emergency tracheal catheter 31).
   c. Hospitalize the patient as soon as possible — (Here ambulance telephone numbers are indicated). (A sketch is further provided to illustrate the laryngostomy technique).

MASK No. 4 — ANAPHYLACTIC SHOCK

Causes

Occurs after injection of penicillin, other antibiotics and practically any drug parentally administered.

Diagnosis

Thready pulse, respiratory distress with/without stridor; dilated pupils, coughing, vomiting, paresthesias, sometimes generalized oedema and uticaria.

Treatment

1. Act immediately
   a. Place in shock position, clear airway;
   b. Get assistant to summon medical help. (Here names and telephone numbers of two doctors are indicated).
2. Inject 0.5–1 ml of a 1:1000 Adrenalin solution (0.5ml for children; 0.25ml for infants). (Here an aperture is provided for the Adrenalin 12);
3. Place an intravenous butterfly needle, secure with adhesive strip and set up an intravenous drip. (Vacoliters available — 37, 38). (Here an aperture is provided for the intravenous butterfly needle 15);
4. By the same route:
   a. inject 100mg Solucortef. (Here an aperture is provided) and
   b. if pulse is weak, mix 1 ampoule of Vasoxine with 5ml of water.
Inject this ml per ml until the pulse improves (titrate). (Here the apertures for the Vasoxine 21 and water 26 are provided).
   c. inject 50ml Phenergan (Aperture for Phenergan 19);
5. Administer oxygen under pressure or give mouth to mouth resuscitation with the aid of the life-saver tube. (Aperture here for tube 24). (See briefcase lid for method);
6. Monitor pulse and observe respiration. Assist breathing as long as it is not sufficient or spontaneous. If the pulse disappears, follow the procedure set out under No. 5: Cardiac arrest;
7. Arrange for transfer to a hospital when patient can, if necessary, receive further treatment. (Here ambulance telephone numbers are indicated).

The above examples should be sufficient to indicate the general principle which is applied in the preferred embodiment of the invention. The text can be duplicated in more than one language, and a preferred feature is the use throughout of one colour printing, e.g. for the English text and throughout a second colour printing for a second appropriate language, e.g. French, Spanish, German or other suitable language for other countries. By way of example, the additional masks which have not been described in detail are a mask for cardiac arrest, a mask for hypoglycemic-coma arising with the history of Diabetes-mellitus, a mask for toxic reaction to local anaesthetic and a mask for treating snake and scorpion bites.

A further feature is an instruction chart fixed onto the inside of the lid of the briefcase, giving instructions on sites for intramuscular injections, details recommended for the shock treatment and position of patient technique for emergency tracheostomy and the technique of mouth to mouth resuscitation.

Although the preferred embodiment of this invention as described is suited for use only by medical practitioners, dentists, nursing sisters and para-medical personnel of similar qualifications, the principle of the invention can be applied in a less professionally advanced embodiment in which all the treatments can be carried out by medical auxiliaries, who do not have the necessary training for such procedures as intravenous injection, emergency tracheostomy and the like. Members of the general public can after a brief scanning of the diagrams and instructions, be of immense value to the person rendering assistance to the collapsed patient.

The following are some of the references upon which the text appearing on the masks is based:

| | | |
|---|---|---|
| 1. Burford J. | - | Emergency in the Dental Surgery, New Zealand Dental Journal 69:300. |
| 2. Cleaton-Jones P. | - | Essential Medicine for Dental Practice, Springfield, Illinois, Thomas 1971. |
| 3. Davies J & Davies I.J.T. | - | The Pathogenesis and Treatment of Shock BR. HOSP. MED.2 686 (1968). |
| 4. Duvenhage J. | - | Postgraduate Course on Emergency Procedures (1969). |
| | - | Personal Communication (1974). |
| 5. Hannington-Kiff J.G. | - | Fainting and collapse in dental practice. Dental Practitioner 20 : 7 (Sept. 1969). |
| 6. Killey H. C. | - | Seaward G. R. K.L.W. An outline of oral surgery parts 1 and 2 Crystal : John Wright and Sons (1971). |
| 7. Lemo J. | - | Management of Clinical Emergencies. Tydskrif van T.V.S.A., vol. 22 No.6 Unic 1967. |
| | - | Personal Communication (1974). |
| 8. Lessing, A.J.P. | - | Personal Communication (74). |
| 9. McCarthy F. M. | - | Emergencies in Dental Practice, Prevention and Treatment. Philadelphia, Toronto : W. R. Saunders (72). |
| 10. Merck Manual of Diagnosis & Therapy | - | 12th edition, RAHWAY: MSD (1972). |
| 11. Morch E. T. | - | Tracheostomy and Mechanical Hyperventilation, Armamentarium 3, 4(1960). |
| 12. Rowe N. L. & Killey H. C. | - | Fractures of the Facial Skeleton, Edinburgh and London : Livingstone (1968). |

What I have said above in regard to humans, applies mutatis mutandis, to animals as well, and this invention is applicable in the veterinary sphere as well.

What is claimed is:

1. An emergency kit comprising means for administering emergency clinical treatment to animals or persons, said means comprising a plurality of articles, said articles comprising drugs and medical instruments, a holder for said articles, a plurality of masks, said holder being adapted to hold each particular article in one particular position in combination with said plurality of different masks, the masks being located in said kit in a manner adapted to permit selection of any one mask from the plurality of masks, the masks being adapted for any such selected mask to be placed one only at a time in one particular masking position to mask some but not all articles in the holder, each mask having openings which are adapted to expose some other articles in the holder, the exposed articles being clinically appropriate to one particular mode of clinical treatment of animals or persons, each mask being identifiable by suitable markings as being appropriate to the particular mode of clinical treatment for which the articles which that mask is adapted to expose in the masking position are appropriate, each particular mode of clinical treatment associated with each mask being appropriate to a definable clinical condition.

2. A kit as claimed in claim 1, in which the openings in each mask are arranged in a sequence from top edge to bottom edge in the use position of the mask, which sequence corresponds substantially with the sequential order in which the articles which are exposed by the openings will be used, in which the openings in the mask are combined with a text relating to the particular treatment, in which the text comprises one or more of the following:

a description of the condition for which the mask is appropriate, a note of causes, an aid to diagnosis and step by step directions for carrying out the appropriate treatment, the directions being adapted to be read from top edge to bottom edge in the use position of the mask.

3. A kit as claimed in claim 1, which is adapted to be conveniently portable, in which the holder comprises a tray-like receptacle in the form of a solid slab having a substantially flush surface with recesses for the articles, including instruments and drugs and any other articles required, which holder is adapted to ensure that articles do not become misplaced by virtue of the recesses being dimensioned to hold the articles firmly in position when the articles are squeezed into the recesses, but with finger holes located adjacent and in communication with the recesses and the flush surface to facilitate removal of the article with finger and thumb.

4. A kit as claimed in claim 1, in which the mask is adapted so that it can only be placed in the correct orientation to mask the holder, and cannot easily be inadvertently placed the wrong way around, by virtue of the perimeter being specially shaped asymmetrically with corresponding asymmetric shape of the holder perimeter which is adapted to receive the mask.

5. A kit as claimed in claim 1, in which the holder has a flat upper surface, with the articles located within recesses in the holder so as to be substantially flush with the flat upper surface, the recesses having finger holes located adjacent and in communication with the recesses and the upper surface, in which the masks comprise flat stiff sheets, located stacked together in means adapted to hold the masks, alongside the holder, the means being adapted to permit removal of any one and all of the masks for purposes of selection of any one mask and placement thereof in a masking position.

6. A kit as claimed in claim 1, in which the openings in each mask are arranged in a sequence from top edge to bottom edge in the use position of the mask, which sequence corresponds substantially with the sequential order in which the articles which are exposed by the openings will be used, in which the openings in the mask are combined with a text relating to the particular treatment, in which the text comprises one or more of the following: a description of the condition for which the mask is appropriate, a note of causes, and aid to diagnosis and step by step directions for carrying out the appropriate treatment, which is adapted to be conveniently portable, in which the holder comprises a tray-like receptacle in the form of a solid slab having a substantially flush surface with recesses for the articles, including instruments and drugs and any other articles required, which holder is adapted to ensure that articles do not become misplaced by virtue of the recesses being dimensioned to hold the articles firmly in position when the articles are squeezed into the recesses, but with finger holes located adjacent and in communication with the recesses and the flush surface to facilitate removal of the article with finger and thumb, said mask being adapted so that it can only be placed in the correct orientation to mask the holder, and cannot easily be inadvertently placed the wrong way around, by virtue of the perimeter being specially shaped asymmetrically with corresponding asymmetric shape of the holder perimeter which is adapted to receive the mask, the masks including one mask appropriate for clinical treatment of each of two or more of the following clinical conditions in persons:

medicinally induced asthma
 angina pectoris and/or myocardial infarction
 angio-neurotic oedema
 anaphylactic shock
 cardiac arrest
 hypoglycemic coma
 toxic reaction to local anaesthetic
 snake or scorpion bites, the articles in the holder being appropriate to the clinical treatments involved.

7. A kit as claimed in claim 6, in which eight masks are provided, appropriate to treatment of all eight clinical conditions listed in claim 6, and the articles in the holder comprise substantially the following:

anti-snakebite serum and scorpion anti-venom
 Adrenalin Injection Bp
 Glyceral-Trinitrate Tablets
 Dextrose Injection Bp
 Butterfly Needles
 Salbutamol
 Hydrocortisone Sodium Succinate
 Promethazine Hydrochloride Injection
 Mepyramine
 Dextrose Injection Bp
 Methoxamine-Hydrochloride
 Theophylline Ethylene Diamine
 Diazepam
 Oral Tube for Mouth to Mouth Resuscitation
 Glyceral-Trinitrate Tablets
 Phial Water for Injections
 2ml Hydrocortisone Sodium Succinate
 4 × 50ml Vials of Sodium Bicarbonate
 2 × 1 ml Vials Pentazocine
 1 × 10ml Vial Calcium-Chloride
 Emergency Tracheal Catheter
 1 × 1ml Vial of Atrophine Sulphate
 1 × 10ml Vial of Water for Injections
 1 × 1ml Vial of Adrenalin
 1 × Sterile Injection Needle
 1 × 1ml Vial Atrophine
 1 × 150ml Bottle Normal Saline for Administration by Venoclysis
 1 × 150ml Bottle Sodium Chloride and Dextrose Injection for Administration by Venoclysis or their pharmacological equivalents.

8. A kit as claimed in claim 1, said masks being freely removable from said kit.

9. A kit as claimed in claim 1, said masks being located in association with the holder in storage positions in which they do not mask the articles in the kit.

* * * * *